United States Patent [19]

Milburn et al.

[11] 4,365,874
[45] Dec. 28, 1982

[54] OCULOTORSIONOMETER

[76] Inventors: Wanda O. Milburn, 1745 Westridge, Ann Arbor, Mich. 48105; T. Dean Clack, 1162 Warrington Dr., Ann Arbor, Mich. 48103

[21] Appl. No.: 186,259

[22] Filed: Sep. 11, 1980

[51] Int. Cl.³ ............................................. A61B 3/02
[52] U.S. Cl. ................................... 351/243; 351/222; 351/237
[58] Field of Search .............................. 351/30, 36, 17

[56] References Cited

U.S. PATENT DOCUMENTS 3,535,026 10/1970 Coss .................................. 351/36 X Primary Examiner—John K. Corbin
Assistant Examiner—Rodney Bovernick
Attorney, Agent, or Firm—Olsen and Stephenson

[57] ABSTRACT

An apparatus for measuring torsional rotation of an eyeball about the visual axis by means of an afterimage. The apparatus includes a frame mountable to a patient so as to be fixed with respect to the patient's skull. Mounted on the frame are means for creating a transitory bright image to imprint the retina of the patient's eye with an afterimage and means for creating a target image alignable with said afterimage. Measuring means is included in the apparatus so as to indicate the angular displacement of the target image relative to a preset reference position corresponding to a different stimulus condition. In the preferred embodiment, the apparatus is a tubular assembly supported by a bite bar.

14 Claims, 5 Drawing Figures

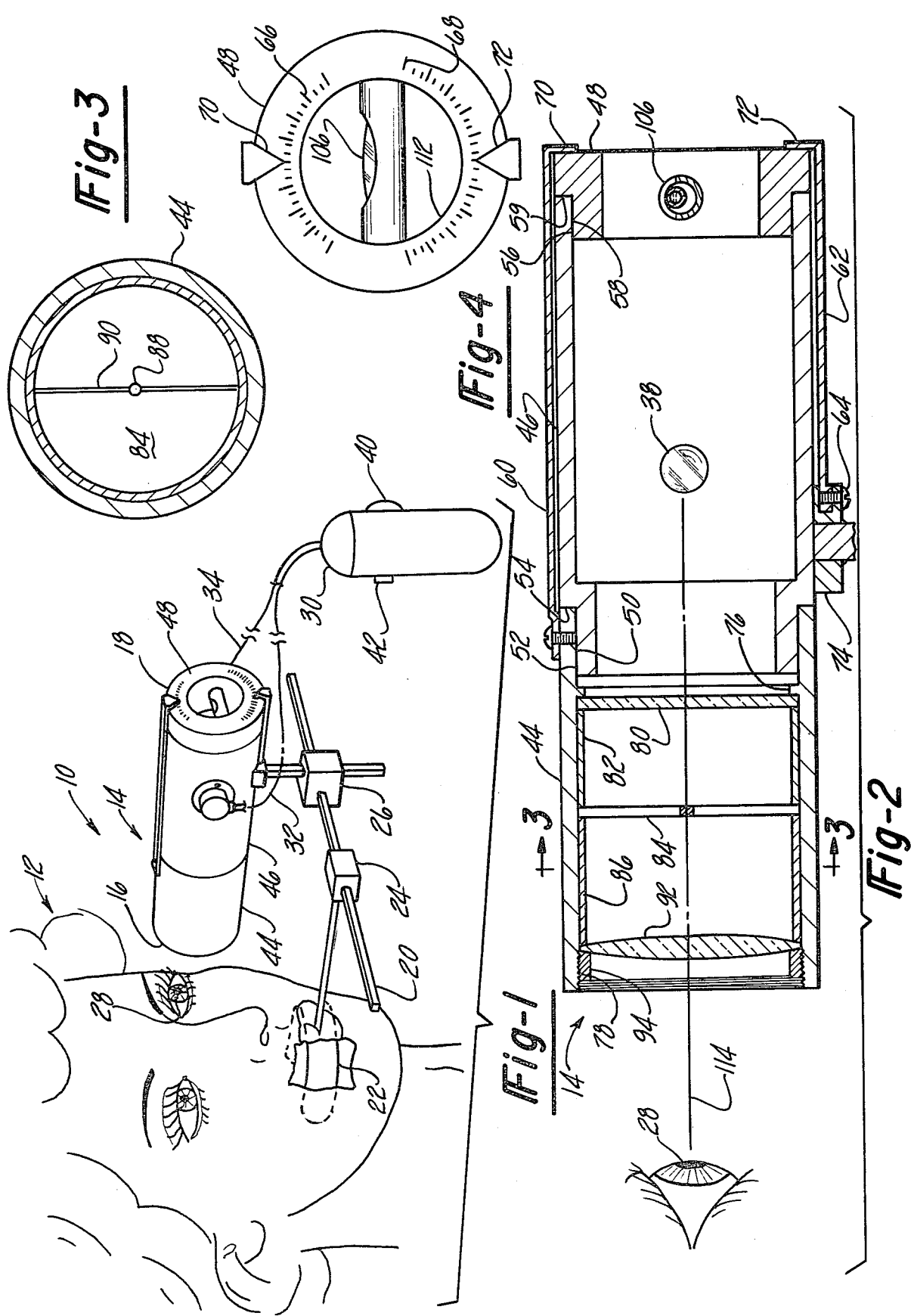

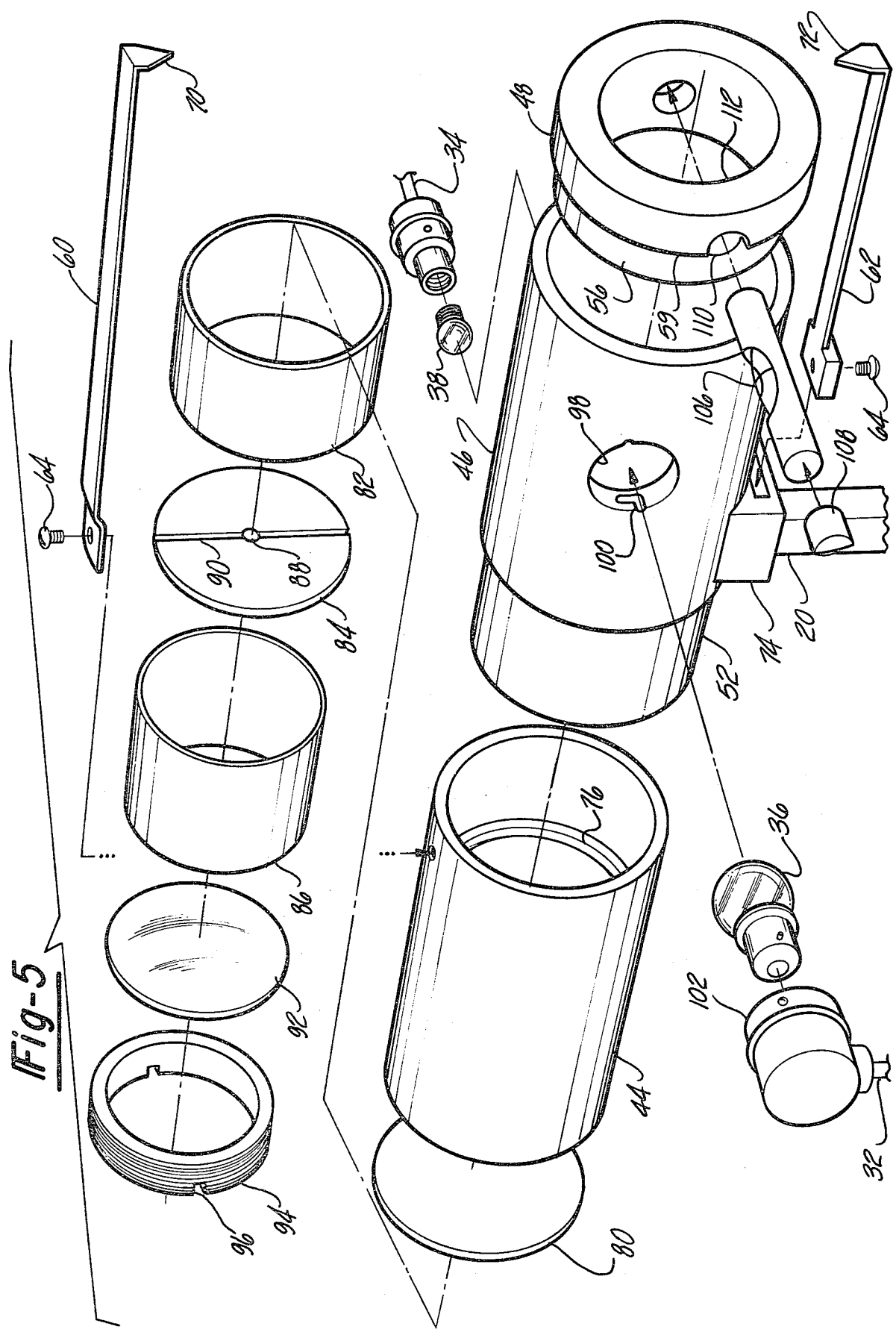

OCULOTORSIONOMETER

BACKGROUND OF THE INVENTION

1. Field of the Invention

The present invention relates to eye examining and testing instruments and, more particularly, to an apparatus for measuring the torsional rotation of an eyeball about the visual axis by means of an afterimage.

2. Description of the Prior Art

Medical and scientific studies have shown that measurements of torsional rotation of an eyeball about the visual axis are useful in identifying the source of certain sensori-neural problems and physical dysfunctions. However, measurements of ocular torsion are not currently utilized in medical applications due to the difficulty of observing ocular torsion and the inapplicability of techniques currently used to determine other types of eyeball motion. No apparatus has been devised which is sufficiently accurate, convenient, and economical for widespread routine clinical application.

Approaches to the measurement of ocular torsion are generally classified as either objective or behavioral. Objective methods utilize the natural or artificial landmarks on the surface of the eyeball in conjunction with an external referent to quantify changes in eyeball position. Reliable objective measurements have been obtained by the use of photographic records of natural landmarks; however, that technique is too time-consuming and costly for widespread routine clinical application. Behavioral methods generally measure ocular torsion by means of an afterimage: the phenomenon that when a person stares at an object for a period of time or sees a bright flash of light, an image of the object or flash of light can be seen afterwards. In afterimage testing, the retina is first imprinted with a line or a cross, a new stimulus condition is then set, and the patient is asked to report the orientation of the afterimage.

Typical of the prior art measurement techniques is the afterimage technique of Jongkees and Groen published in the Journal of Laringology and Otology, vol. 64, pages 135–140, 1950. A patient was instructed to focus on a line of vertical light for one minute to create an afterimage. Then, the patient's head was rotated about the dorsoventral axis by means of a special rotatable chair and the patient was asked to assist the tester to indicate the position of the afterimage on a separate white target screen. The tester held a ruler in front of the screen and rotated it according to the patient's instructions until the patient stated that the ruler was aligned with the afterimage. A similar technique was utilized by applicant Milburn in 1970 wherein reflected light from a flashbulb was substituted to imprint the afterimage.

Both the objective and behavioral techniques of the prior art have been too costly, inaccurate, or inconvenient for anything except very limited experimental use. It is therefore an object of the present invention to provide an apparatus for accurately and conveniently measuring ocular torsion and which is suitable for routine clinical application.

SUMMARY OF THE INVENTION

The present invention is an apparatus which measures the torsional rotation of an eyeball about the visual axis by means of afterimage oculotorsionometry. The apparatus of the present invention includes a frame which is fixed with respect to the patient's skull and which can utilize a simple bite bar secured by the patient's teeth and jaw. A means for creating a transitory bright image visable to the patient is mounted directly on the frame to create an afterimage. A target image means is rotatably mounted on the frame for rotation about the visual axis in axial alignment with the afterimage after the patient receives a new stimulus condition. The target image means engages a measuring means so as to indicate the angular displacement of the target means relative to a preset reference position.

The apparatus of the present invention includes in a convenient single device several functions which in the past have required clumsy separate devices and includes several unique features with substantial advantages over the prior art. The attachment of the afterimage light source to the skull by means of a bite bar framework assures proper alignment of the eye and afterimage light source without necessitating sophisticated rotatable chairs and remote afterimage devices. The use of a single image screen for both the afterimage and the target image increases the accuracy of the torsional measurement by eliminating the need for the patient to shift his/her gaze from the afterimage device to a separate target device. Further, the intermittent illumination of the target image greatly facilitates comparison with the afterimage. Unlike the devices in the prior art, the apparatus of the present invention utilizes a constant focallength lens and centering spot to improve the orientation and quality of the afterimage and the target image. The measuring means can include pointers and arcuate scales which permit direct reading of the angular displacements of the image screen and of the apparatus itself relative to gravity. And, the present invention utilizes a remote control operable by a tester while measuring the angular displacements.

As a result of the present invention, ocular torsion can be easily and accurately measured by a compact, self-contained, tube-shaped device which is supported by a bite bar and is infinitly adjustable by the patient. Further objects, features, and advantages of this invention will become apparent from a consideration of the following description, the appended claims and the accompanying drawings.

BRIEF DESCRIPTION OF THE DRAWINGS

FIG. 1 is a perspective view of the oculotorsionometer of this invention shown in relation to a patient being examined by the device;

FIG. 2 is a cross-sectional view of the oculotorsionometer taken along a lengthwise plane as viewed from the side;

FIG. 3 is a cross-sectional view taken along the plane 3—3 of FIG. 2;

FIG. 4 is a rear view of the tubular assembly of the oculotorsionometer; and

FIG. 5 is an exploded view showing the elements of the oculotorsionometer.

DESCRIPTION OF THE PREFERRED EMBODIMENT

With reference to the drawing, the oculotorsionometer of the present invention, indicated generally at 10, is illustrated in FIG. 1 in operating relation to a patient, indicated generally at 12. The oculotorsionometer includes a tubular assembly 14 having a front end 16 and rear end 18, a simple support structure of horizontal and vertical bars 20, a bite bar mouthpiece 22, and adjustment clamps 24 and 26 for positioning the tubular assembly 14 in front of either of the patient's eyes 28. The bite bar mouthpiece 22 has a rigid frame and a deformable covering operable to gain and hold impressions of the patient's teeth.

A hand-held control unit 30 is connected by means of wires 32 and 34 to a flash bulb 36 and a low luminance bulb 38 within the tubular assembly 14, as shown in FIG. 5, to permit a person testing the patient to control the bulbs 36 and 38 while observing the patient and the tubular assembly 14. The control unit 30 has a trigger button 40 and a reset button 42 positioned on the surface of the control unit 30 for convenient engagement by the tester's thumb. A battery and flasher within the control unit 30 are connected to the buttons 40 and 42 by means of conventional circuitry so as to power bulbs 36 and 38 sequentially, as described below.

The tubular assembly 14 consists of a front tubular member 44, a rear tubular member 46, and a level calibration indicator 48 which are axially aligned and rotatably connected as shown in FIG. 2. An internal surface 50 adjacent the rear of the front tubular member 22 telescopes over a center sleeve 52 extending forward from the rear tubular member 46 and forms a sliding fit therewith. A shoulder 54 resulting from the juncture of the center sleeve 52 and the rear tubular member 46 longitudinally restrains the front tubular member 44 by slideably engaging the rear surface thereof. The level calibration indicator 48 includes a rear sleeve 56 which slides within the internal surface 58 of the rear tubular member 46 to maintain axial alignment and includes a flange 59 which slideably engages the rear edge of the rear tubular member 46 to restrict longitudinal movement.

Pointer arms 60 and 62 are secured to the front and rear tubular members 44 and 46, respectively, by means of two machine screws 64. These pointer arms 60 and 62 extend longitudinally along the outer surface of the rear tubular member 46 and the level calibration indicator 48 and extend radially along the rear surface of the level calibration indicator 48 so as to engage upper and lower arcuate scales 66 and 68 as two pointers 70 and 72. In the preferred embodiment shown, pointer arms 60 and 62 are offset somewhat from the outer cylindrical surface of the rear tubular member 46 to facilitate rotation of the front tubular member 44 and to prevent interference with the operation of the pointers 70 and 72.

The radially extending pointers 70 and 72 slideably engage the rear surface of the level calibration indicator 48 so as to restrict longitudinal movement of the level calibration indicator 48 with respect to either the front or the rear tubular members 44 or 46. The rear tubular member 46 is secured to the horizontal and vertical bars 20 by means of a base 74 which incorporates a mounting for the pointer arm 62. Thus, the front and rear tubular members 44 and 46 and the level calibration indicator 48 are maintained in a desired axial and longitudinal orientation with respect to the patient's eye 28 and yet are independently rotatable.

The inner surface of front tubular member 44 includes an inwardly extending shoulder 76 adjacent the forward edge of the center sleeve 52 and internal threads 78 adjacent the front edge of the front tubular member 44 to facilitate the mounting of internal elements. A disk-shaped diffuser 80 is composed of translucent material and is secured against the shoulder 76 by a rear cylindrical spacer 82. A screen 84 is secured against the rear spacer 82 by a front spacer 86. As shown in FIGS. 3 and 5, the screen 84 consists of an opaque disk having a luminous paint spot 88 at the center of the disk and a narrow slit 90 across the diameter of the disk excepting only the luminous paint spot 88. Alternatively, the screen may be formed by etching the narrow slit 90 in a disk of metal-clad transparent material. A constant focal length convex lens 92 is secured to the front sleeve 86 by an externally threaded sleeve 94 having wrench slots 96 to facilitate rotational installation engaging the internal threads 78. Thus, by means of the shoulder 76, the front and rear spacers 86 and 82, and the externally threaded sleeve 94, the diffuser 80, the screen 84, and the lens 92 are secured transversely and are spaced longitudinally within the front tubular member 44.

The rear tubular member 46 includes an opening 98 with bayonet-type grooves 100 for receiving a bulb socket 102 which holds the flash bulb 36. Similarly, an opening with bayonet-type grooves is provided in the rear tubular member 46 for receiving the bulb socket 104 holding the low luminance bulb 34. The bulb sockets 102 and 104 are mounted on the sides or bottom of the rear tubular member 46 rather than the upper portion thereof so as to avoid interference with the pointer arm 60. A conventional bubble level 106 is positioned within the level-calibration indicator 48 so as to be transverse of the rear tubular member 46 along a diameter thereof. The bubble level 106 is secured by a cylindrical plug 108 which is inserted into the opening 110 and is appropriately shaped to conform to the rear sleeve 56 and the flange 59 of the level-calibration indicator 48. The internal opening 112 of the level-calibration indicator 48 is cylindrical to permit viewing of the bubble of the bubble level 106 and to inspect or verify the proper operation of bulbs 32 and 34.

With the oculotorsionometer in place and the patient's head positioned at a predetermined angle, the patient is directed to observe a dimly illuminated spot resulting from diffused ambient light passing through the lens 92 to the luminous paint spot 88; the tube chamber is otherwise dark. While the patient gazes at that spot, thereby aligning his/her visual axis 114 with the center line of the tubular assembly 14, the person testing the patient engages the trigger button 40 of the hand-held control 30 to cause flash bulb 36 to emit a bright flash of light and to thereafter cause the low luminance bulb 38 to begin blinking. The bright flash is restricted by the diffuser 80 and the screen 84 and is enlarged and focused by the lens 92 so as to appear to the patient as a bright line extending across the diameter of the tubular assembly 14 intersecting the dimly illuminated spot. This line of bright light marks the retina of the patient's eye with an afterimage. The patient next sees a dim line of light intersecting the dimly illuminated spot and resulting from the blinking light of the low luminance bulb 38 projecting through the screen 84 for comparison to the afterimage. Next, a new stimulus condition is set, for example, the rotation of the patient's head to a different predetermined angle. The patient then rotates the front tube 22 until the dimly blinking line coincides with the afterimage.

The pointer arms 60 and 62 are designed such that they indicate the angular displacement of the front tubular member 44 and are usable by the tester positioned in front of and facing the patient. The pointer 72 of the lower pointer arm 62 engages the lower arcuate scale 68 to indicate the angular orientation of the rear tubular member 46 and the patient's skull with respect to gravity when the bubble of the bubble level 106 is properly centered by rotation of the level-calibration indicator 48 by the tester. In the preferred embodiment shown, the pointer 70 of the pointer arm 60 engages the upper arcuate scale 66 to show the angle of the slit 90 of the screen 84 with respect to gravity when the bubble of the bubble level 106 is properly centered. Alternatively or additionally, the pointer arm 60 could engage an arcuate scale mounted directly on the rear tubular member 46 so as to directly show the angular displacement of the front tubular member 44 relative to the rear tubular member 46 between the two stimulus positions.

It will be seen from the foregoing description of the preferred embodiment of the invention that it performs accurate and convenient measuring of ocular torsion and is suitable for routine clinical application as well as experimental use. While the preferred embodiment has been described in considerable detail, the present invention is not to be limited to such detail except as may be necessitated by the appended claims.

What is claimed is:

1. An oculotorsionometer for measuring torsional rotation of a patient's eyeball about the visual axis of the eyeball comprising:
    a frame mountable to the patient so as to be fixed with respect to the patient's skull,
    afterimage means mounted on said frame so as to create a transitory bright image visible to the patient for imprinting the retina of the patient's eye with an afterimage,
    target image means visible to the patient and rotatably mounted on said frame for rotation about said visual axis so as to permit the patient to align a target image with said afterimage, and
    measuring means engaged by said target image means so as to indicate the angular displacement of said target image means relative to a preset reference position.

2. An oculotorsionometer as defined in claim 1 which further comprises a tube in general alignment with said visual axis and enclosing said afterimage means and said target image means.

3. An oculotorsionometer as defined in claim 1 wherein said afterimage means includes a flash means and a screen which permits only a predetermined pattern of light to pass from said flash means to the patient's eye.

4. An oculotorsionometer as defined in claim 3 wherein said target image means includes said screen and a discontinuous low luminance light source illuminating said predetermined pattern.

5. An oculotorsionometer as defined in claim 4 which further includes a power cord and remote control unit for hand-held control of said flash bulb and said low luminance light source.

6. An oculotorsionometer as defined in claim 5 wherein said control unit is sequentially operable to excite said flash means and immediately thereafter initiate blinking of said low luminance light source.

7. An oculotorsionometer as defined in claim 4 wherein said screen includes a spot centrally located with respect to said predetermined pattern for directing the patient's gaze so as to align said visual axis with said predetermined pattern before exciting said flash means.

8. An oculotorsionometer as defined in claim 4 which further comprises a lens of constant focal length positioned between the patient's eye and said screen in alignment with said visual axis to enhance the visibility of said afterimage means and said target means.

9. An oculotorsionometer as defined in claim 1 wherein said frame includes a bite bar for fixing the apparatus to the patient's skull by gripping of the bite bar by the patient's teeth and jaw.

10. An oculotorsionometer as defined in claim 9 wherein said frame includes brackets for horizontal and vertical adjustments to position said afterimage means and said target image means in front of either eye and wherein said bite bar includes a mouthpiece having a rigid structure and a pliable covering to gain and hold impressions of the patient's teeth.

11. An oculotorsionometer as defined in claim 1 wherein said measuring means includes a pointer and an arcuate scale visible from a viewpoint facing the patient along the visual axis.

12. An oculotorsionometer as defined in claim 1 wherein said measuring means includes an indication of the angular displacement of the target means relative to gravity.

13. An oculotorsionometer for measuring torsional rotation of a patient's eyeball about the visual axis of the eyeball comprising:
    a frame having a bite bar for fixing the apparatus to the patient's skull by gripping of the bite bar by the patient's teeth and jaw,
    a tube adjustably mounted on said frame so as to be positioned in front of either eye of the patient in alignment with said visual axis,
    a screen rotatably mounted within said tube for rotation about said visual axis, said screen having a transparent portion so as to permit a predetermined pattern of light to pass,
    flash means mounted within said tube in alignment with said visual axis so as to flash a bright light through said screen onto the patient's eye for imprinting the retina of the patient's eye with an afterimage of said predetermined pattern,
    a discontinuous low luminance light source mounted within said tube in alignment with said visual axis so as to shine through said screen and repeatedly project a target image visable to the patient for comparison to said afterimage, and
    measuring means engaged by said screen so as to indicate the angular displacement of said screen with respect to a preset reference position when said screen is rotated about said visual axis so as to align said target image and said afterimage.

14. In a method for measuring the torsional rotation of a patient's eyeball, the steps comprising:
    fixing a frame to the patient's skull,
    providing means on said frame for imprinting the retina of the patient's eyeball with an afterimage line,
    providing means on said frame for aligning a target image line with said afterimage line, and
    providing measuring means on said frame for indicating the angular displacement of said target image line relative to a preset reference position.

* * * * *